(12) United States Patent
Zallat et al.

(10) Patent No.: US 10,156,514 B2
(45) Date of Patent: Dec. 18, 2018

(54) DEVICE FOR COMPENSATING FOR THE DRIFT OF A PHASE SHIFT OF A DEVICE FOR MODULATING THE POLARIZATION STATE OF A LIGHT BEAM

(71) Applicants: Centre National de la Recherche Scientifique—CNRS, Paris (FR); Universite de Strasbourg, Strasbourg (FR)

(72) Inventors: Jihad Zallat, Ostwald (FR); Marc Torzynski, Strasbourg (FR); Alex Lallement, Fegersheim (FR); Christian Heinrich, Illkirch (FR)

(73) Assignees: CENTRE NATIONAL DE LA RECHERCHE SCIENTIFIQUE-CNRS, Paris (FR); UNIVERSITE DE STRASBOURG, Strasbourg (FR)

( * ) Notice: Subject to any disclaimer, the term of this patent is extended or adjusted under 35 U.S.C. 154(b) by 184 days.

(21) Appl. No.: 14/899,966

(22) PCT Filed: Jun. 20, 2014

(86) PCT No.: PCT/FR2014/051539
§ 371 (c)(1),
(2) Date: Dec. 18, 2015

(87) PCT Pub. No.: WO2015/004358
PCT Pub. Date: Jan. 15, 2015

(65) Prior Publication Data
US 2016/0139033 A1     May 19, 2016

(30) Foreign Application Priority Data
Jul. 10, 2013 (FR) ..................... 13 56803

(51) Int. Cl.
*G01N 21/23* (2006.01)
*G02B 27/00* (2006.01)
(Continued)

(52) U.S. Cl.
CPC ............. *G01N 21/23* (2013.01); *G01N 21/21* (2013.01); *G02B 5/3016* (2013.01);
(Continued)

(58) Field of Classification Search
CPC .................. G01N 21/21; G01N 21/23; G01N 2201/0636; G01N 2201/0683; G01J 4/00;
(Continued)

(56) References Cited

U.S. PATENT DOCUMENTS 3,866,038 A * 2/1975 Korth ................... G01B 11/303
                                                          250/236
5,658,490 A * 8/1997 Sharp ................... G02F 1/13363
                                                       252/299.01

(Continued)

FOREIGN PATENT DOCUMENTS

CN          101216616       7/2008

OTHER PUBLICATIONS

Jihad Zallat, Marc Torzynski, and Alex Lallement, "Double-pass self-spectral-calibration of a polarization state analyzer," Opt. Lett. 37, 401-403 (2012).*
(Continued)

*Primary Examiner* — Violeta A Prieto
(74) *Attorney, Agent, or Firm* — Brinks Gilson & Lione; John C. Freeman

(57) ABSTRACT

A device for analyzing and/or generating a polarization state of a measurement point of a target object includes a polarizer suitable for selecting, in an incident light wave, a light beam which is linearly polarized in a predefined direction; a first birefringent element suitable for having the light beam pass
(Continued)

Figure 1:
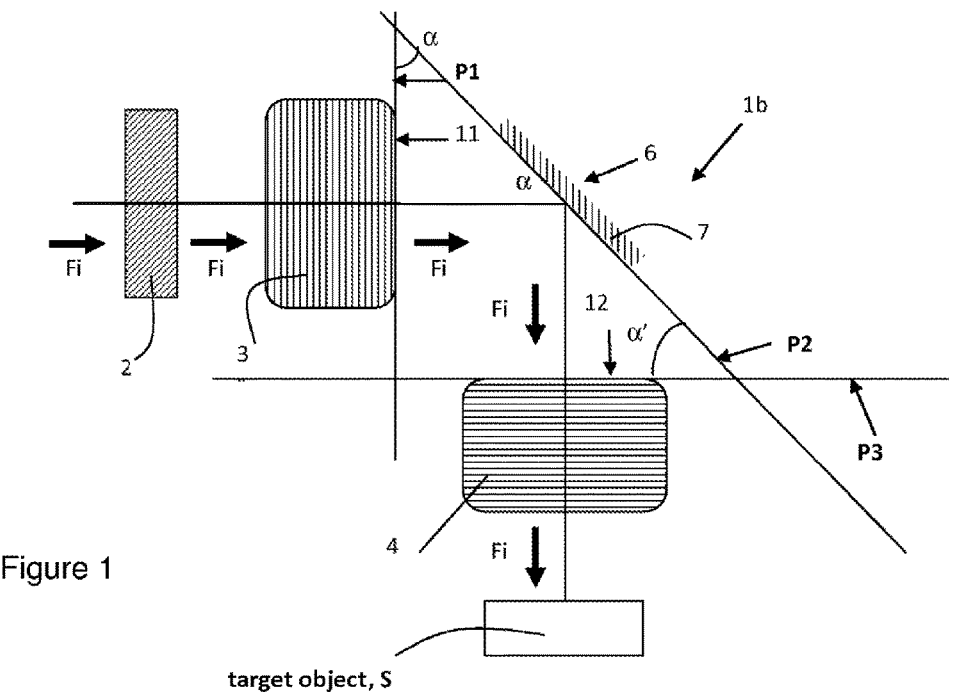

therethrough; a second birefringent element identical to the first element and suitable for having the light beam pass therethrough, the light beam then being directly or indirectly directed toward the object in order to be reflected in the form of a reflected beam. The device includes an optical assembly having one or more optical elements located in an optical path between the first element and the second element, and the optical assembly includes an odd number of mirrors, or, an odd number of half-wave plates, or, an odd number of a mix of mirrors and half-wave plates.

11 Claims, 3 Drawing Sheets

(51) Int. Cl.
G02B 27/28 (2006.01)
G02B 5/30 (2006.01)
G01N 21/21 (2006.01)
G01J 4/00 (2006.01)

(52) U.S. Cl.
CPC ....... *G02B 5/3083* (2013.01); *G02B 27/0025* (2013.01); *G02B 27/286* (2013.01); *G01J 4/00* (2013.01); *G01N 2201/0636* (2013.01); *G01N 2201/0683* (2013.01)

(58) Field of Classification Search
CPC .............. G02B 27/0025; G02B 27/286; G02B 5/3016; G02B 5/3083
See application file for complete search history.

(56) References Cited

U.S. PATENT DOCUMENTS

| 6,711,311 | B2* | 3/2004 | Delisle | G02B 6/12004 385/11 |
| 6,765,635 | B1* | 7/2004 | Kelly | G02F 1/0136 349/102 |
| 6,795,184 | B1 | 9/2004 | Herzinger | |
| 2002/0171793 | A1* | 11/2002 | Sharp | C09K 19/0225 349/117 |
| 2004/0130717 | A1 | 7/2004 | Drevillon | |
| 2005/0179980 | A1* | 8/2005 | Iwatsuka | G02F 1/09 359/280 |
| 2015/0241632 | A1* | 8/2015 | Chann | G02B 6/2706 385/27 |
| 2015/0331205 | A1* | 11/2015 | Tayebati | G02B 6/4206 385/27 |

OTHER PUBLICATIONS

First Office Action dated Nov. 28, 2016 (26 pages including English translation) out of Chinese priority Application No. 201480038234.3.

Dubreuil et al., Mueller matrix polarimetry for improved liver fibrosis diagnosis, Optics Letters, Mar. 15, 2012, Optical Society of America, US—ISSN 0146-9592, vol. 37, No. 6, pp. 1061-1063, XP001574562.

International Search Report dated Sep. 30, 2014 out of corresponding PCT priority application No. PCT/FR2014/051539 (6 pages).

Written Opinion dated Sep. 30, 2014 out of corresponding PCT priority application No. PCT/FR2014/051539 (6 pages).

McIntyre, *Achromatic Wave Plates for the Visible Spectrum*, Journal of the Optical Society of America, vol. 58, No. 12, Dec. 1968, pp. 1575-1580.

Rabinovich, *Experimental research of temperature influence on retardance in crystal quartz for deep ultraviolet range of wavelength*, Optical Engineering, vol. 46 (2), Feb. 2007, pp. 026501-1-026501-5.

Woźniak, *Adjustment method of an imaging Stokes polarimeter based on liquid crystal variable retarders*, Applied Optics, Jan. 10, 2011, vol. 50, No. 2, pp. 203-212.

Terrier, *Robust estimation of Stokes parameters with a partial liquid-crystal polarimeter under thermal drift*, Applied Optics, vol. 53, Issue 29, 2014, pp. 6706-6712.

Tiwary, Estimation of order parameter of a liquid crystal variable retarder using Haller's approximation, Applied Optics, vol. 56, No. 14, May 10, 2017, pp. 4180-4184.

* cited by examiner

DEVICE FOR COMPENSATING FOR THE DRIFT OF A PHASE SHIFT OF A DEVICE FOR MODULATING THE POLARIZATION STATE OF A LIGHT BEAM

This application claims priority to International Application No. PCT/FR2014/051539 filed Jun. 20, 2014 and to French Application No. 1356803 filed Jul. 10, 2013; the entire contents of each are incorporated herein by reference.

FIELD OF THE INVENTION

The present invention relates generally to devices for analyzing and/or generating a polarization state of a measurement point of a target object.

More particularly, it relates to an analyzing and/or generating applied to the medical field.

STATE OF THE ART

In the field, a device for analyzing and/or generating a polarization state of a measurement point of a target object is already known, the device comprising:
a polarizer suitable for selecting, from an incident light waves, a light beam rectilinearly polarized in a predefined direction,
a first birefringent element suitable for being passed through by said light beam,
a second birefringent element identical to the first element and suitable for being passed through by said light beam, said light beam then being intended to be directed directly or indirectly toward said object to be reflected in the form of a reflected radiation.

The first and second birefringent elements suitable for being passed through by the light beam are sensitive to the conditions of their environment. As an example, the first and second elements can be sensitive to temperature, which entails repeated calibration procedures each time the analysis and/or generation device is used. The purpose of these calibration procedures is to correct the effects of the temperature drift of one of the first and second birefringent elements.

More generally, since the first and second elements are sensitive to environmental conditions, phase drift may occur between the first and second birefringent elements which then requires time-consuming calibration procedures to be carried out in order to compensate for this drift.

OBJECT OF THE INVENTION

In this context, the issue posed here is to propose a device for analyzing and/or generating a polarization state that reduces the time devoted to the calibration of this device.

The solution proposed by the present invention is for an optical assembly, consisting of one or more optical elements, to be situated on an optical path lying between the first element and the second element, the optical assembly consisting of:
an odd number of mirrors, or,
an odd number of half-wave plates, or,
an odd combined number of mirrors or half-wave plates.

In one embodiment of the invention, the first element and/or the second element is:
a rotationally mobile birefringent plate, or
a nematic liquid crystal element.

In another embodiment of the invention, the device further comprises a light source suitable for emitting a light beam, said light source being suitable for emitting a beam upstream of the polarizer.

In another embodiment of the invention:
the first element comprises a first face extending in a first plane orthogonal to the direction of the light beam propagation Fi, said mirror extending in a second plane secant by an angle $\alpha$ of between 20° and 80° relative to the first plane,
the second element comprises a third face extending in a third plane orthogonal to the direction of the light beam propagation Fi, the second and third planes being secant by an angle of angle $\alpha'$ equal, in value, to $\alpha$.

In one embodiment, the optical assembly comprises an even number plurality of birefringent elements.

According to one embodiment, the device further comprises a photosensitive sensor suitable for converting the reflected beam into an electrical signal.

According to a second object of the invention, another aim is a method for generating a polarization state of a measurement point of a target object comprising the following steps:
selecting, from incident light waves, an incident beam rectilinearly polarized in a predefined direction,
passing successively through a first birefringent element then a second birefringent element with said incident beam,
directly or indirectly directing the beam upstream of the second birefringent element toward said object which then emits a reflected beam.

The method further comprises a step consisting in compensating for the phase drift of said first and second elements by the inclusion of an optical assembly, consisting of one or more optical elements, situated on an optical path of the beam lying between said first and second elements, the optical assembly consisting of:
an odd number of mirrors, or,
an odd number of half-wave plates, or,
an odd combined number of mirrors or half-wave plates.

According to a third object of the invention, another aim is a method for analyzing a polarization state of a measurement point of a target object comprising the following steps:
emitting a reflected beam from said object and directing it directly or indirectly downstream of the second birefringent element,
passing successively through the second birefringent element, then a first birefringent element, with said reflected beam,
converting the reflected beam into an electrical signal.

The method further comprises a step consisting in compensating for the phase drift of said first and second elements by the inclusion of an optical assembly, consisting of one or more optical elements on an optical path of the beam lying between said first and second elements, the optical assembly consisting of:
an odd number of mirrors, or,
an odd number of half-wave plates, or,
an odd combined number of mirrors or half-wave plates.

Figure 2:
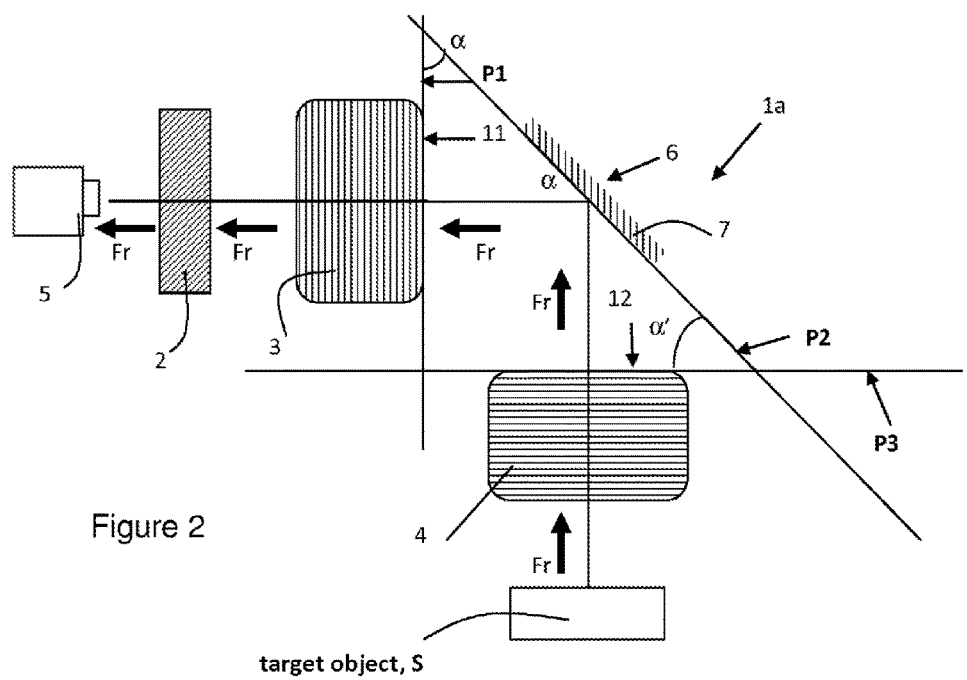
Figure 3:
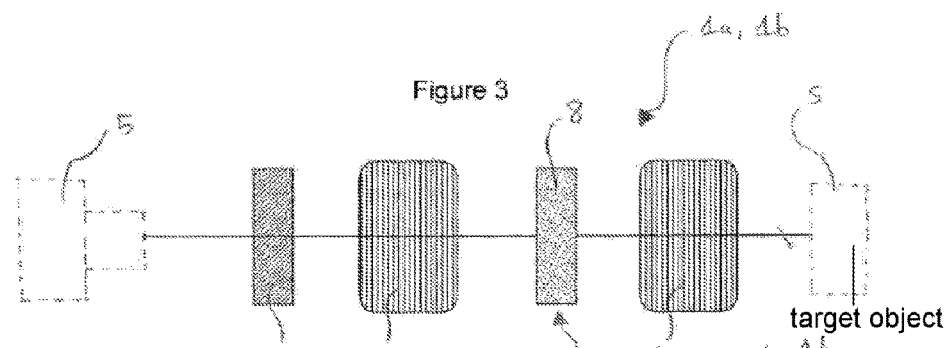
Figure 4:
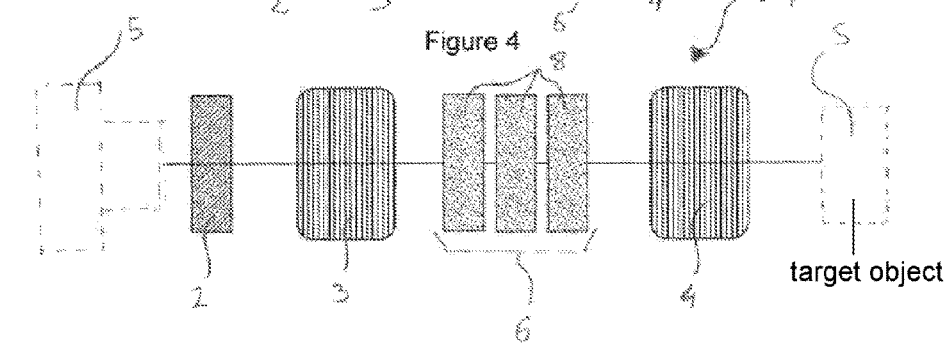
Figure 5:
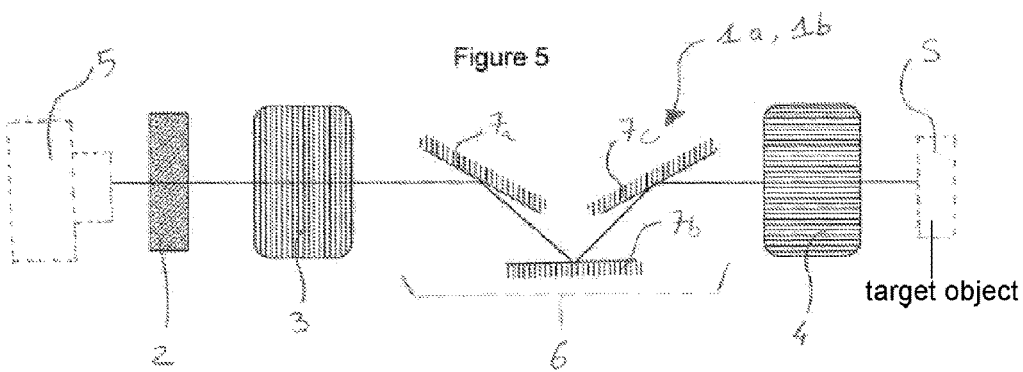
Figure 6:
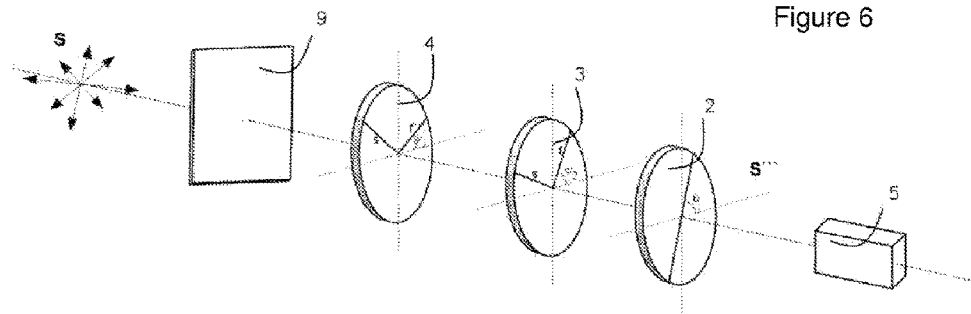
Figure 7:
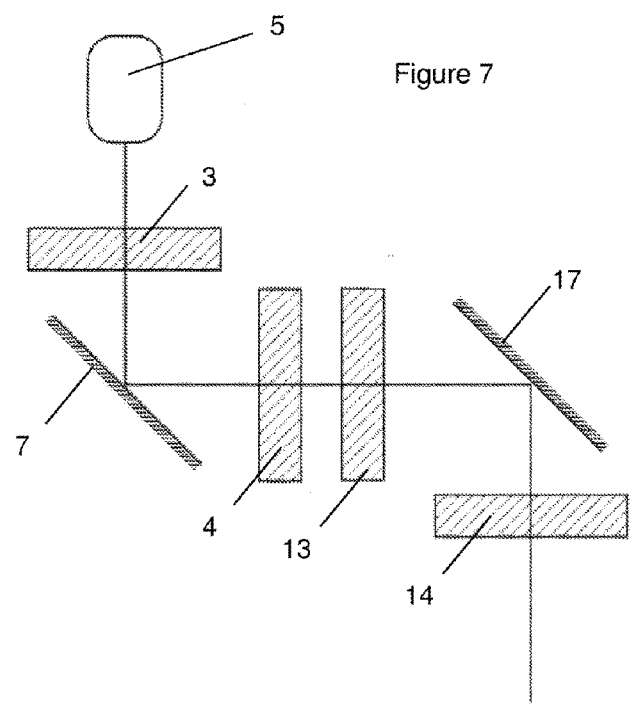

Other features and advantages will also emerge from the description which is given hereinbelow, in an indicative and nonlimiting manner, with reference to the attached drawings, in which:

FIG. 1 shows a theoretical diagram of an exemplary device for generating a polarization state in which the optical assembly consists of a mirror, FIG. 2 shows a theoretical diagram of an exemplary device for analyzing a polarization state in which the optical assembly consists of a mirror, FIG. 3 shows a theoretical diagram of an exemplary device for analyzing and/or generating a polarization state in which the optical assembly consists of a half-wave plate, FIG. 4 shows a theoretical diagram of an exemplary device for analyzing and/or generating a polarization state in which the optical assembly consists of three half-wave plates, FIG. 5 shows a theoretical diagram of an exemplary device for analyzing and/or generating a polarization state in which the optical assembly consists of three mirrors, FIG. 6 shows a theoretical diagram of an exemplary device for analyzing and/or generating a polarization state according to the prior art and in which the angular orientations $\theta$, $\psi_1$ and $\psi_2$ are referenced, FIG. 7 shows a theoretical diagram of an exemplary device for complete analysis and/or generation of a polarization state which uses the proposed architecture twice.

THEORETICAL JUSTIFICATION

Referring to the figure, in the case of a device for analyzing a polarization state of a measurement point of a target object, it is possible to measure the polarization of the light originating from a target object by accessing the Stokes vector of the light originating from each pixel of the object. This is done by the use of birefringent elements such as rotationally mobile quarter-wave plates or nematic liquid crystal elements offering the advantage of requiring no mechanical element and allowing acquisition rates close to the video rate.

In a configuration for analyzing a polarization state, the polarization state of the light originating from the polarizer to the photosensitive sensor S''' is described, after its passage through the various optical elements, by the product of the Mueller matrix of the entire system (product of the Mueller matrices of the optical elements which make up the device for analyzing a polarization state) with the incoming Stokes vector S.

The polarization of the light beam originating from the incident light waves is therefore described after its passage through the various optical elements by the product of the Mueller matrices thereof and then results in the relationship:

$$S''' = M_P(\theta) \cdot M_R(\delta_2, \psi_2) \cdot M_R(\delta_1, \psi_1) \cdot S$$

$M_R(\delta_1, \psi_1)$ and $M_R(\delta_2, \psi_2)$ are the Mueller matrices of the first and second birefringent elements and $M_P(\theta)$ is the Mueller matrix of the polarizer. $\psi_1$, $\psi_2$ are the orientations of the rapid axes of the first and second birefringents relative to the horizontal axis. $\theta$ corresponds to the orientation of the linear polarizer. $\delta_1$, $\delta_2$ are the phase shifts obtained by applying the voltages V1 and V2. These phase shifts are desired. Phase drifts are added to these phase shifts, and it is these phase drifts which have to be corrected.

S''' conventionally has four components I''', Q''', U''' and V'''. These correspond to the components of the Stokes vector to be measured, notably the intensity I''' which corresponds to the intensity measured by the photosensitive sensor. It will be noted that:

$$(I''', Q''', U''', V''') = (s_0, s_1, s_2, s_3)$$

S has four components I, Q, U and V. The intensity I originating from the object is expressed in the form:

$$I(\delta_1, \delta_2, \psi_1, \psi_2, \theta) = s_0 + f(\delta_1, \delta_2, \psi_1, \psi_2, \theta) \cdot s_1 + g(\delta_1, \delta_2, \psi_1, \psi_2, \theta) \cdot s_2 + h(\delta_1, \delta_2, \psi_1, \psi_2, \theta) \cdot s_3 \qquad (I)$$

The Stokes parameters of the waves originating from the object can be obtained by choosing phase shifts and orientations which characterize the device for analyzing a polarization state, namely the parameters $\delta_1$, $\delta_2$, $\psi_1$, $\psi_2$, and $\theta$. In practice, the orientations $\psi_1$, $\psi_2$, and $\theta$ are chosen in order to maximize the modulation of the intensity from the device for analyzing a polarization state.

Thus, the proposed solution consists in positioning, between the first and second birefringent elements, an optical assembly consisting of:
- an odd number of mirrors, or,
- an odd number of half-wave plates, or,
- an odd combined number of mirrors or half-wave plates.

Thus constructed, the optical assembly has a Mueller matrix which has the following form:

$$M_I = \begin{pmatrix} 1 & 0 & 0 & 0 \\ 0 & 1 & 0 & 0 \\ 0 & 0 & -1 & 0 \\ 0 & 0 & 0 & -1 \end{pmatrix}$$

The polarization of the light beam originating from the incident light waves described after its passage through the various optical elements further comprising the optical assembly by the product of the Mueller matrices thereof then results in the relationship:

$$S''' = M_P(\theta) \cdot M_P(\delta_2, \psi_2) \cdot M_I \cdot M_R(\delta_1, \psi_1) S$$

It is then appropriate to choose $\psi_1$, $\psi_2$, and $\theta$ so as to maximize the modulation of the intensity of the analysis device.

By way of example, starting from the relationship (I) and by choosing the orientations $\theta = \pi/2$, $\psi_1 = \pi/8$ and $\psi_2 = 3\pi/8$, the measured intensity is given by:

$$I(\delta_1, \delta_2, \psi_1, \psi_2, \theta) = \frac{3}{4} \cdot (2 \cdot s_0 - s_1 - s_2 + (-s_1 + s_2) \cdot \cos(\delta 1 - \delta 2) + \sqrt{2} \cdot s_3 \cdot \sin(\delta 1 - \delta 2)).$$

In this case, if the temperature changes from $T_0$ to $T_1$, $\delta_1$ deflects by $\Delta_1$ and $\delta_2$ deflects by $\Delta_2$. Since the first and second birefringent elements are identical, it can be considered that $\Delta_1 = \Delta_2$.

Thus, the arrangement of an optical assembly as mentioned above on an optical path lying between the first element and the second element advantageously makes it possible to reveal the expression $(\delta 1 - \delta 2)$ in the expression of $I(\delta_1, \delta_2, \psi_1, \psi_2, \theta)$, which makes it possible to eliminate the drifts $\Delta_1$ and $\Delta_2$ from this expression and therefore to eliminate certain calibration procedures designed to determine them. The phase drift (due for example to a variation of the temperature) of the first element is compensated by the phase drift of the second element $(\delta 1 + \Delta_1 - \delta_2 - \Delta_2 = \delta 1 - \delta 2)$.

DESCRIPTIONS OF EXEMPLARY EMBODIMENTS

Referring to FIGS. 1 to 5, these figures show a light source S suitable for emitting incident light waves, and a device 1a, 1b for analyzing and/or generating a polarization state of a measurement point of a target object which comprises:
- a polarizer 2 suitable for selecting, from incident light waves, an incident light beam $F_i$ rectilinearly polarized in a predefined direction, a first birefringent element 3 suitable for being passed through by said incident light beam $F_i$ and by a reflected beam $F_r$ which is reflected by the target object, a second birefringent element 4 identical to the first element 3 and suitable for being passed through by said incident light beam $F_i$ and by the reflected light beam $F_r$, said incident light beam $F_i$ being intended to be directed directly or indirectly toward said object to be reflected in the form of said reflected light beam $F_r$, a photosensitive sensor 5 suitable for converting the reflected light beam $F_r$ into an electrical signal.

Also present are means for computing the polarization information from the reflected light beam $F_r$ reflected by the target object.

Hereinafter in the description, the incident light beam $F_i$ is called "incident beam $F_i$" over the entire path from the light source to the target object and "reflected beam $F_r$" over the entire path from the target object to the sensor 5.

The light source S is intended to emit an incident light beam $F_i$ rectilinearly polarized in a predefined direction. This light source S can, for example, consist of a laser diode or of a wideband source of the halogen lamp type.

Conventionally, this light source S suitable for emitting a light beam is associated with a polarizer 2, upstream thereof.

The polarizer 2 is situated downstream of the light source so that it can select, from incident light waves, a rectilinearly polarized light beam. It is then suitable for being passed through by the incident light waves.

An optical assembly 6, consisting of one or more optical elements, is situated on an optical path lying between the first element 3 and the second element 4, the optical assembly 6 consisting of:

an odd number of mirrors 7, or, an odd number of half-wave plates 8, or, an odd combined number of mirrors 7 or half-wave plates 8.

In FIGS. 1 to 5, the first birefringent element 3 is arranged between the polarizer 2 and the optical assembly 6, on the optical path of the light beam. The second birefringent element 4 is arranged between the optical assembly 6 and the light source S.

In one embodiment of the invention, the first birefringent element 3 is a rotationally mobile birefringent plate. Preferentially, the birefringent plate is a delay plate. The first birefringent element 3 can also be a nematic liquid crystal element.

In one embodiment of the invention, the second birefringent element 4 is a rotationally mobile birefringent plate. Preferentially, the birefringent plate is a delay plate. The second birefringent element 4 can also be a nematic liquid crystal element.

The first and second birefringent elements 3, 4 are both delay plates or both nematic liquid crystal delay units.

The first and second birefringent elements 3, 4 define delay units. Preferentially, they are liquid crystal delay units. Each of these first and second birefringent elements 3, 4 makes it possible to modify the polarization state of the incident beam without requiring mechanical actions on the device, such as rotations for example. The estimation of the Stokes parameters is more accurate and faster. The control variable parameter of these first and second birefringent elements is a delay 5. This delay 5 is controlled by the effective value of a voltage adjusted, using a computer, via a control board.

In one embodiment, the optical assembly 6 comprises an even number plurality of birefringent elements. For each pair of birefringent elements, a first member of said pair is situated upstream of the optical assembly having a Mueller matrix given by $$MI = \begin{pmatrix} 1 & 0 & 0 & 0 \\ 0 & 1 & 0 & 0 \\ 0 & 0 & -1 & 0 \\ 0 & 0 & 0 & -1 \end{pmatrix},$$

and the second member of this pair is situated downstream of this optical assembly 6 having the same Mueller matrix MI.

Preferentially, the analysis 1a and/or generation 1b device comprises precisely two birefringent elements 3, 4. The use of two birefringent elements 3, 4 is justified by the fact that the polarimetric measurement matrix $P(\delta_i,\psi,\theta)$ is ill-suited $(I_i=P(\delta_1,\psi,\theta)\cdot S)$ whatever the number and the value of the delays $\delta_i$.

FIG. 1 shows, in a polarization state generation configuration, that the incident light waves pass through the polarizer 2 which selects an incident beam $F_i$ rectilinearly polarized in a predefined direction.

The incident beam $F_i$ passes successively through the first birefringent element 3 to be reflected by the optical assembly 6 consisting of the mirror 7 which is situated on the optical path lying between the second element 4 and the first element 3. The incident beam $F_i$ then passes through the second birefringent element 4.

FIG. 2 shows, in a polarization state analysis configuration, that the reflected beam passes successively through the second birefringent element 4, then is reflected by the optical assembly 6 consisting of the mirror 7 which is situated on the optical path lying between the second element 4 and the first element 3, passes through the first birefringent element 3 which is followed by the polarizer 2. The resulting light intensity is then measured by a photosensitive sensor suitable for converting the radiation reflected by the target object into an electrical signal.

It can be seen that the beam reflected by the target object has an optical path that passes successively through the second birefringent element 4, before being directed toward the optical assembly 6 having the Mueller matrix MI and defined by a mirror 7, then passing through the first birefringent element 3 which is followed by the polarizer 2. At the end of the optical path, the photosensitive sensor 5 can convert the reflected beam $F_r$ into an analog electrical signal. This signal can then be amplified, then digitized by an analog-digital converter, and processed by the polarization information computation means, in order to analyze the polarization state of a measurement point of the target object.

Advantageously, the analysis and/or generation device 1a, 1b can comprise a monochromatic filter 9 in order to center the incident light waves on a predetermined wavelength.

FIGS. 1 and 2 show solutions in which the optical assemblies 6 consist of mirrors 7. The principle of the compensation of the phase drift of the first and second elements 3, 4 is therefore to introduce, on the optical path, between the first and second birefringent elements 3, 4, one or more optical elements which introduce a global phase shift of n radians. This phase shift of n radians has the effect of compensating the phase drift of the first birefringent element 3 by the phase drift of the second birefringent element 4.

FIGS. 3 and 4 show solutions for which the optical assembly 6 consists of half-wave plates. The optical path taken is differentiated in that the incident and reflected beams pass through the half-wave plates. As can be seen in FIGS. 3 and 4, the principle of the analysis and/or generation of the polarization state is the same, but the orientation given to the optical path is different. The use of mirrors 7 will influence the angular orientation of the optical path on either side of the optical assembly 6, that is to say at the input and at the output. Conversely, the use of half-wave plates does not modify the angular orientation of the optical path on either side of the optical assembly 6, that is to say at the input and at the output. For example, a beam passing through a half-wave plate in its position of use will have a rectilinear trajectory from the input and after the output of the optical assembly 6.

In these conditions, the use of half-wave plates (FIGS. 3 and 4) is suitable for an in-line configuration, when the spectral band is narrow, whereas the use of mirrors 7 (FIGS. 1, 2 and 5) is particularly suitable for a multi-spectral configuration or wideband measurements.

In the embodiment represented in FIG. 3, the optical assembly 6 consists of a half-wave plate.

In the embodiment represented in FIG. 4, the optical assembly 6 consists of three successive half-wave plates. They face one another.

The odd number of half-wave plates between the first and second birefringent elements is here essential since the aim is to introduce a global phase-shift of n radians.

According to an embodiment shown in FIGS. 1 and 2, the first element 3 comprises a first face 11 extending in a first plane (P1) orthogonal to the direction of the light beam propagation Fi, said mirror 7 extending in a second plane (P2) offset by an angle α of between 20 and 80° relative to the first plane (P1). The second element 4 comprises a third face 12 extending in a third plane (P3) orthogonal to the direction of the light beam propagation Fi, the second and third planes (P2, P3) being offset by an angle α' equal, in value, to α.

In an embodiment shown in FIG. 5, a device for analyzing and/or generating a, 1b polarization state is represented in which the optical assembly 6 consists of three mirrors 7. More specifically, the mirrors 7 are oriented such that the light beam is successively reflected by a first mirror 7a, then a second mirror 7b and then a third mirror 7c. By virtue of the odd number of mirrors, the Mueller matrix MI is of the desired form. The use of several mirrors 7 makes it possible to vary the angle between the mirrors 7 and adapt the optical assembly to a housing of the machine in which the analysis and/or generation device is installed.

In an embodiment shown in FIG. 7, an analysis and/or generation device 1a, 1b is represented in which four birefringent elements 3, 4, 13, 14 are used.

More specifically, a third birefringent element 13 is facing a second birefringent element 4, on the optical path of the light beam. The light beam is then intended to be directed directly or indirectly toward a second mirror 17 to be reflected. Consequently, the light beam is reflected (at least) a second time. Facing the second mirror 17, on the optical path of the light beam reflected by the second mirror 17, there is arranged a fourth birefringent element 14. This configuration guarantees an optimal conditioning of the instruments for measuring the polarization. The polarizer 2 can be arranged, upstream of the first birefringent element 3 or downstream of the fourth birefringent element 14 depending on whether the device 1a, 1b is intended to analyze a polarization state of a measurement point of the target object or to generate a polarization state of a measurement point of the target object.

The invention claimed is:

1. A device for analyzing and/or generating a polarization state of a measurement point of a target object, the device comprising:
    a polarizer suitable for selecting, from incident light waves, a light beam rectilinearly polarized in a predefined direction,
    a first birefringent element suitable for being passed through by the light beam,
    a second birefringent element identical to the first birefringent element and suitable for being passed through by the light beam, the light beam then being intended to be directed directly or indirectly toward the object to be reflected in the form of a reflected beam,
    wherein a phase of the first and second birefringent elements shifts depending on an environmental condition,
    wherein an optical assembly, consisting of one or more optical elements, is situated on an optical path lying between the first birefringent element and the second birefringent element, and is adapted to compensate for the phase shift of the first and second birefringent elements, the optical assembly consisting of:
    an odd number of mirrors, or,
    an odd number of half-wave plates, or,
    an odd combined number of mirrors and half-wave plates.

2. The device as claimed in claim 1, wherein the first birefringent element and/or the second birefringent element is a rotationally mobile birefringent plate, or a nematic liquid crystal element.

3. The device as claimed in claim 1, wherein the device comprises a light source suitable for emitting a light beam, the light source being suitable for emitting a beam upstream of the polarizer.

4. The device as claimed in claim 1, wherein:
    the optical assembly consists of one mirror;
    the first birefringent element comprises a first face extending in a first plane orthogonal to a direction of the light beam propagation Fi, the mirror extending in a second plane secant by an angle α of between 20° and 80° relative to the first plane,
    the second birefringent element comprises a third face extending in a third plane orthogonal to the direction of the light beam propagation Fi, the second and third planes being secant by an angle of angle α' equal, in value, to α.

5. The device as claimed in claim 1, wherein the optical assembly comprises an even number of birefringent elements.

6. The device as claimed in claim 1, wherein the device further comprises a photosensitive sensor suitable for converting the reflected beam into an electrical signal.

7. A method for generating a polarization state of a measurement point of a target object comprising:
    selecting, from incident light waves, an incident beam rectilinearly polarized in a predefined direction,
    passing successively through a first birefringent element then a second birefringent element with the incident beam,
    directly or indirectly directing the beam upstream of the second birefringent element toward the object which then emits a reflected beam, wherein a phase of the first and second birefringent elements shifts depending on an environmental condition, and compensating for the phase shift of the first and second birefringent elements by the inclusion of an optical assembly consisting of one or more optical elements situated on an optical path of the beam lying between the first and second birefringent elements, the optical assembly consisting of:

an odd number of mirrors, or, an odd number of half-wave plates, or, an odd combined number of mirrors and half-wave plates.

8. A method for analyzing a polarization state of a measurement point of a target object comprising:

emitting a reflected beam from the object and directing it directly or indirectly downstream of a second birefringent element, passing successively through the second birefringent element, then a first birefringent element, with the reflected beam, wherein a phase of the first and second birefringent elements shifts depending on an environmental condition, and converting the reflected beam into an electrical signal, compensating for the phase shift of the first and second birefringent elements by the inclusion of an optical assembly consisting of one or more optical elements on an optical path of the beam lying between the first and second birefringent elements, the optical assembly consisting of:

an odd number of mirrors, or, an odd number of half-wave plates, or, an odd combined number of mirrors and half-wave plates.

9. The device according to claim 1 wherein the environmental condition is temperature.

10. The device according to claim 7 wherein the environmental condition is temperature.

11. The device according to claim 8 wherein the environmental condition is temperature.

\* \* \* \* \*